(12) United States Patent
Minagawa et al.

(10) Patent No.: US 6,350,273 B1
(45) Date of Patent: *Feb. 26, 2002

(54) CORNEUM PUNCTURE NEEDLE

(75) Inventors: Hirotaka Minagawa; Hiroki Tsuruta; Yasuyoshi Matsumoto; Narushi Ito, all of Tokyo (JP)

(73) Assignee: NEC Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/265,834

(22) Filed: Mar. 10, 1999

(30) Foreign Application Priority Data

Mar. 11, 1998 (JP) .......................... 10-059479

(51) Int. Cl.$^7$ ............................... A61B 17/34
(52) U.S. Cl. ..................... 606/186; 606/185
(58) Field of Search ................ 606/181, 183, 606/185, 186, 188, 116, 189; 81/9.22

(56) References Cited

U.S. PATENT DOCUMENTS

| | | | | |
|---|---|---|---|---|
| 234,881 A | * | 11/1880 | McAlpine | |
| 4,712,548 A | * | 12/1987 | Enstrom | 606/181 |
| 5,366,470 A | * | 11/1994 | Ramel | 606/183 |
| 5,611,809 A | * | 3/1997 | Marshall et al. | 606/181 |
| 5,913,868 A | * | 6/1999 | Marshall et al. | 606/181 |

FOREIGN PATENT DOCUMENTS

| | | |
|---|---|---|
| JP | 4-341241 | 11/1992 |
| JP | 6-130916 | 5/1994 |
| JP | 7-132119 | 5/1995 |
| JP | 9-51878 | 2/1997 |
| JP | 9-140687 | 6/1997 |

* cited by examiner

*Primary Examiner*—Michael H. Thaler
(74) *Attorney, Agent, or Firm*—Young & Thompson

(57) ABSTRACT

A corneum puncture needle for extracting tissue fluid from under the skin corneum includes a needle body and a stylus extending from the needle body to be inserted into a corneum of a human body. The stylus and the needle body form therebetween a stepped portion acting as a stopper when the stylus is inserted into a corneum of a human body. The needle body has a core formed in a unitary body with the stylus and a coating layer or a tube formed on the core. The stylus has a suitable length for prevention of damage of blood vessel. A plurality of puncture needles may be arranged on a holder.

10 Claims, 3 Drawing Sheets

CORNEUM PUNCTURE NEEDLE

BACKGROUND OF THE INVENTION (a) Field of the Invention

The present invention relates to a corneum puncture needle used in a device for measuring chemical components contained in effusion or exuded body fluid from human tissue, and more particularly to the structure of a puncture needle used in a corneum puncture device for obtaining tissue fluid from under the skin corneum.

(b) Description of the Related Art

Measurement of chemical components in the human body such as glucose and lactic acid is medically important. Conventionally, such measurement has mainly been carried out through measurement of components in collected blood. The concentration of each component is measured through, for example, observed changes in color and light absorption of test paper, or detection of an electrical signal from a biosensor that converts the concentration into an electrical signal. Blood collection is usually carried out by use of a collecting needle, which is caused to puncture a vein or blood vessel in an arm of a human body. However, such puncturing involves the examinee experiencing physical pain and apprehension.

Recent improvements in measurement apparatuses enable the components in the human body to be measured using a sample of as small as a few microliters. Accordingly, there has been developed a method for collecting blood in which a thin collecting needle having a diameter of a few tens of micrometers is inserted into a blood capillary in order to collect blood. An example of such a method is described in, for example, Patent Publication No. JP-A-95-132119. However, there is a disadvantage in the blood collecting device described in this publication in that the hollow needle made from a silicon nitride film having a thickness on the order of 1 micrometer ($\mu$m) is very brittle. In this respect, there exists the possibility that the needle is bent in the course of puncturing the skin, resulting in closure of the through-hole of the needle, as well as the possibility of the needle breaking off to be left in the body. Further, since blood contains red cells having a diameter as large as 10–20 $\mu$m, when the red cells are passed through a thin tube having a diameter of a few tens of micrometers, hematolysis (rupturing of red cells) occurs, with the result that the concentrations of chemical substances in blood change.

Meanwhile, there has been developed another method in which, in place of conventionally used blood, effusion or exuded fluid collected from the skin surface is used in order to measure components within the human body. This method is reported in, for example, Proc. of the First Pan Pacific Symposium, Vancouver, Canada, July, 57–58, 1986, and Proc. of the 35th Meeting of Japan Society of Medical Electronics and Biological Engineering, 474, 1996.

Effusion is a small amount of fluid obtained through depressurization and suction of a portion of a skin surface from which the corneum has been removed, and is considered to be interstitial fluid or fluid effused from the wall of a capillary vessel by means of filtration under reduced pressure. Since effusion is lower in protein concentration compared to blood, in a measurement using a sensor, only a small amount of protein adheres to the surface of the sensor, resulting in increase of the service life of the sensor. Further, since effusion is collected through the skin, use of effusion is advantageous over collection of blood, in terms of reduction of pain imparted to the examinee and prevention of infection with pathogenic bacteria. This method is described in Patent Publication Nos. JP-A-92-341241, JP-A-97-51878, JP-A-97-140687.

In the method described in JP-A-92-341241, the corneum at a portion of the skin from which effusion is to be collected is first removed through use of an adhesive tape (hereinafter referred to as a "tape stripping method"), and effusion is then obtained through depressurization and suction. However, the removal of the corneum by the tape stripping method involves the following problems.

A first problem is that the removal of the corneum by the tape stripping method requires considerable skill. Corneum thickness and the degree of ease in removing the corneum vary with location on the human body, the age and sex of the examinee, and the like. When removal of the corneum is insufficient, effusion cannot be collected. On the other hand, when removal of the corneum is excessive, bleeding occurs with resultant pain. Therefore, a considerable level of skill is required for removing the corneum to a degree that enables collection of effusion without causing bleeding.

A second problem is that even a skilled person requires 30 minutes or more to remove the corneum by the tape stripping method. During this period, the examinee must be motionless.

A third problem is that a portion of the skin from which the corneum has been removed requires about two weeks for regeneration.

A fourth problem is that in the tape stripping method, since adhesive tape does not contact uniformly with the skin, the corneum is difficult to remove uniformly, possibly resulting in decreased efficiency in collecting effusion.

The problems involved in the method described in JP-A-92-341241 can be solved through employment of the method described in JP-A-97-51878, in which the skin surface is punctured and the punctured portion is suctioned to collect effusion. However, the puncturing/suction device described in JP-A-97-51878 has a problem in that a puncturing needle does not effectively penetrate through the corneum, due to the uneven structure of the skin surface and deformation of the skin upon receipt of puncturing pressure. Simply increasing the length of the puncturing needle and puncturing pressure increases the degree of invasion into the skin, however, without effective collection of effusion.

JP-A-97-140687 describes a method of suctioning and collecting effusion through direct insertion of a hollow needle into the skin, whereas JP-A-97-510879 originated from an International Application describes a method of collecting interstitial fluid by use of a medical needle or the like. However, in order to insert a needle into the skin, these methods require a complicated apparatus for controlling the puncturing pressure and puncturing depth of the needle. Therefore, these methods involve the problem of employing expensive apparatus, as well as the problem of difficulty in collecting effusion. Further, the method of collecting effusion by use of a hollow needle involves the problem that effusion cannot be collected efficiently, due to viscosity of effusion.

SUMMARY OF THE INVENTION

It is therefore an object of the present invention to provide a corneum puncture needle capable of effectively collecting effusion substantially without deformation of skin surface and damaging blood vessel.

The present invention provides corneum puncture needle including a needle body and a stylus extending from the needle body to be inserted into a corneum of a human body, the stylus and the needle body forming therebetween a stepped portion acting as a stopper when the stylus is inserted into a corneum of a human body.

In accordance with the corneum puncture needle of the present invention, the stepped portion functions as a stopper, which enables the stylus to penetrate the corneum without damaging vein or blood vessel while preventing the skin surface from deformation. Thus, effusion can be collected with ease.

DESCRIPTION OF THE PREFERRED EMBODIMENTS

Now, embodiments of the present invention will be described in more detail with reference to the accompanying drawings.

Figure 1:
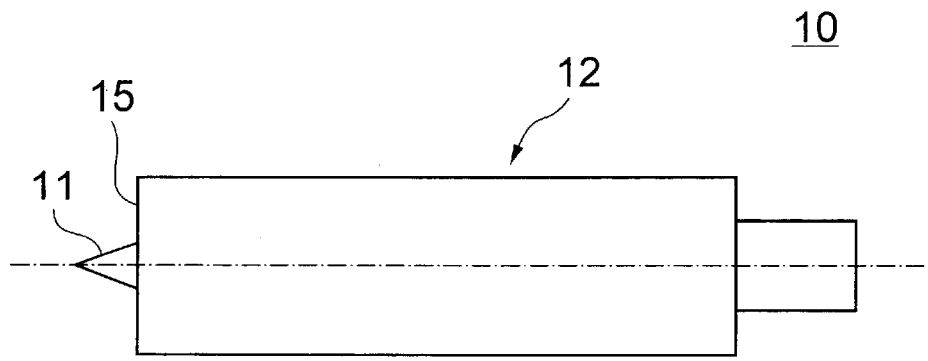
FIG. 1 is a schematic side view of a corneum puncture needle according to a first embodiment of the present invention.

First Embodiment:

Referring to FIG. 1, a corneum puncture needle, generally designated by numeral 10, according to a first embodiment of the present embodiment includes a stylus 11 and a needle body 12, which are formed in a unitary body with each other by, for example, casting. The stylus 11 has a sharp, circular conical or pyramidal shape or a fine circular columnar or rectangular columnar shape. The stylus 11 and the front end 15 of the needle body 12 form therebetween a stepped structure. The stylus 11 extends from the front end 15 of the needle body 12 by a length that enables a hole to be formed in only the corneum of a human body substantially without causing damage to blood vessels.

The projection length of the stylus 11 from the front end 15 of the needle body 12 is preferably set at 0.2 mm or less, in order to cause a hole to penetrate the corneum without damaging blood vessels when the corneum puncture needle 10 of the present embodiment is used to collect effusion from the examinee's forearm. Further, in order to prevent puncture into the corneum, the front end 15 of the needle body 12 preferably has a diameter of 0.5 mm or greater.

The stylus 11 and the needle body 12 may be made of a metal (e.g., Al, Cu, Au, brass, stainless steel, or alloy) or hard plastic (e.g., polycarbonate, polyvinyl chloride, or polypropylene). When hard plastic is used, the corneum puncture needle 10 can be mass-produced at low cost.

The corneum puncture needle 10 of the present embodiment can form a hole only in the corneum, substantially without invasion of the stylus into capillary vessels or subcutaneous tissue cells, thereby facilitating collection of effusion through suction under reduced pressure.

Second Embodiment

Figure 2:
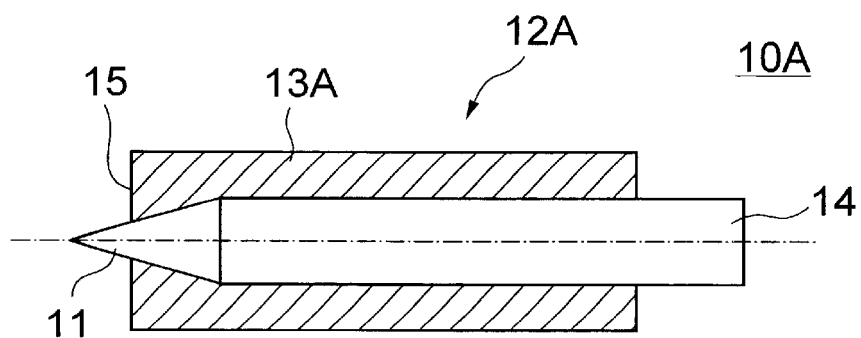
FIG. 2 is a longitudinal sectional view of a corneum puncture needle according to a second embodiment of the present invention.

As shown in FIG. 2, a corneum puncture needle, generally designated by 10A, according to the present embodiment, includes a stylus 11 and a needle body 12A, which has a core 14 formed in a unitary body with the stylus 11 and a coating layer 13A formed on the core 14. The stylus 11 and the front end 15 of the coating layer 13A form therebetween a stepped structure. In the present embodiment, the stylus 11 and the core 14 are implemented as a needle made of stainless steel. Similar needles are used in the following embodiments. The coating layer 13A may be made of any suitable material, such as resin, metal, or rubber. According to the present embodiment, the length of the projecting portion of the stylus 11 extending from the front end 15 of the needle body 12 and the outer diameter of the coating layer 13A can be selected in any combination with ease, which is more advantageous than the structure of the first embodiment, in which the stylus and the needle body are formed in a unitary body.

Third Embodiment

Figure 3:
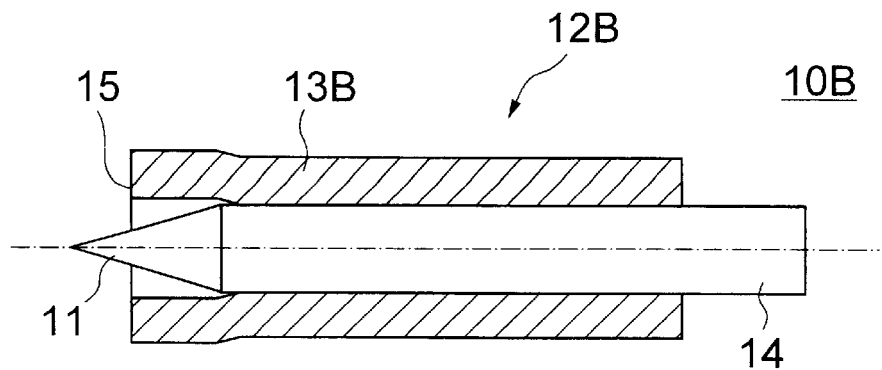
FIG. 3 is a longitudinal sectional view of a corneum puncture needle according to a third embodiment of the present invention.

As shown in FIG. 3, in a corneum puncture needle, generally designated by 10B, according to the present embodiment, the needle body 12B has a core 14 similar to that in the second embodiment and a tube 13B formed on the core 14. The stylus 11 and the core 14 are implemented by a needle, which is inserted into the tube 13B, and the axial position of the needle is adjusted such that the stylus 11 projects from the front end 15 of the tube 13B by a predetermined length. The tube 13B is mechanically fixed to the core 14 of the needle through caulking or press fitting. This affords a lower fabrication cost for the corneum puncture needle.

Fourth Embodiment

Figure 4:
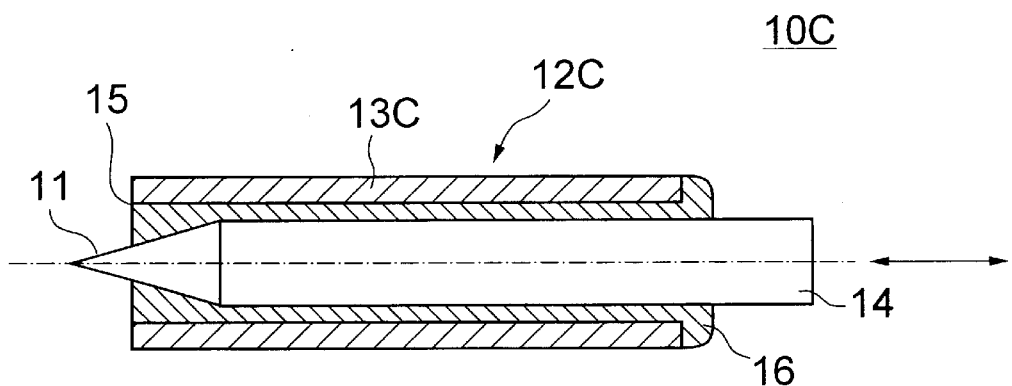
FIG. 4 is a longitudinal sectional view of a corneum puncture needle according to a fourth embodiment of the present invention.

As shown in FIG. 4, in a corneum puncture needle of the present embodiment, generally designated by 10C, in place of the mechanical fixing method described above, an adhesive layer 16 is used for fixing the needle to the tube 13C. In fabrication, adhesive is applied to the needle, which is then inserted into the tube 13C. Subsequently, the needle is axially reciprocated over a distance of, for example, 5 mm such that the adhesive extends uniformly over the entire inner surface of the tube 13C. Further, the axial position of the needle is adjusted such that the stylus 11 projects from the front end 15 of the tube 13C by a predetermined length. Thereafter, the adhesive is hardened so as to fix the needle to the tube 13C. The adhesive may be of any suitable type. Although epoxy resin adhesive (one-part type or two-part type) is preferably used, an instantaneous adhesive such as cyanoacrylate adhesive may also be used. When the needle is fixed to the tube 13B by use of a mechanical fixing such as caulking in the second embodiment, a force acts on the needle during the fixing operation, resulting in that the projecting amount of the needle may change by an amount of a few hundred microns. By contrast, in the bonding structure of the present embodiment, no force acts on the needle when the needle is fixed to the tube 13C, resulting in a small variation in the projection amount of the needle as low as 10 μm or less.

Fifth Embodiment

Figure 5:
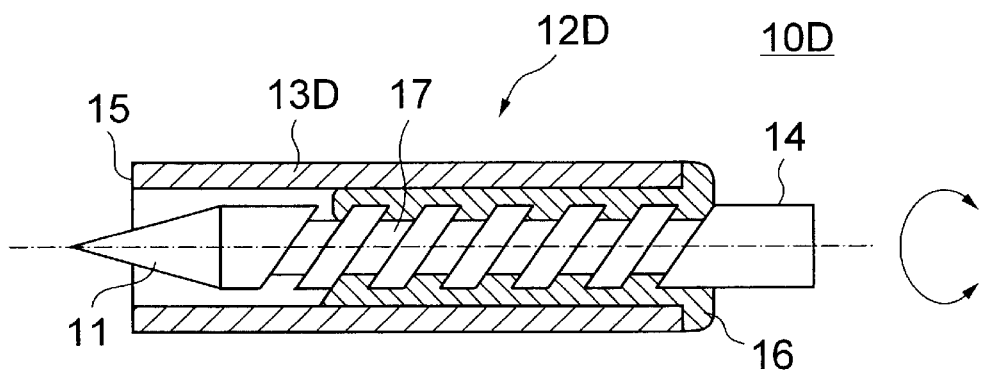
FIG. 5 is a longitudinal sectional view of a corneum puncture needle according to a fifth embodiment of the present invention.

As shown in FIG. 5, a corneum puncture needle of the present embodiment, generally designated by 10D, is similar to the fourth embodiment except that a spiral groove 17 is formed on the core 14 of the needle body 12D for controlling the flow of adhesive. When the needle is rotated after application of adhesive onto the needle and subsequent insertion of the needle into the tube 13D, the adhesive flows along the groove 17 of the needle, resulting in that the adhesive extends uniformly along the groove 17 over the entire inner surface of the tube 13D. Further, the axial position of the needle is adjusted such that the stylus 11 projects from the front end 15 of the tube 13D by a predetermined length. Subsequently, the adhesive is hardened so as to fix the needle to the tube 13D. The area of application of the adhesive can be controlled by rotation of the needle. This prevents the adhesive from flowing out from the front end 15 of the tube 13D to result in a shortened projection amount of the stylus 11 or cause a change in the diameter of the stylus.

Sixth Embodiment

Figure 6:
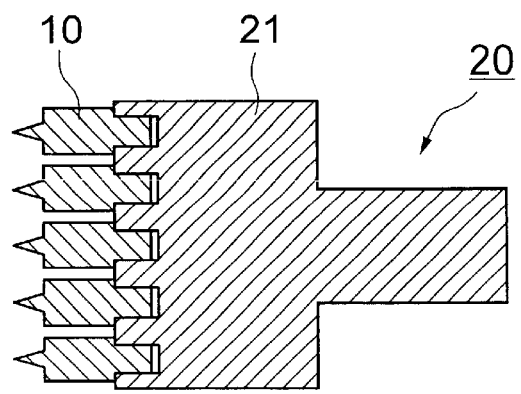
FIG. 6 is a longitudinal sectional view of a corneum puncture member according to a sixth embodiment of the present invention.

FIG. 6 shows a corneum puncture device, generally designated by 20, according to the present embodiment. The corneum puncture device 20 includes a holder 21 and a plurality of corneum puncture needles 10 of the first embodiment, for example, arranged and mounted on the front surface of the holder 21. The corneum puncture device 20 according to the present embodiment provides a large number of holes in the corneum at a time.

Figure 7:
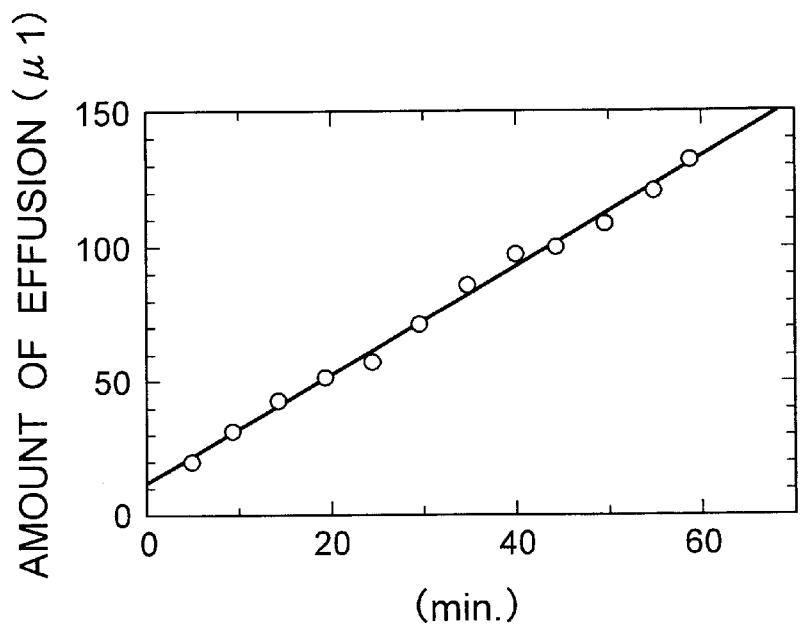
FIG. 7 is a graph showing collection rate of effusion.

Effusion was collected by using the corneum puncture device shown in FIG. 6. Specifically, the corneum puncture device 20 shown in FIG. 6 was used to puncture the skin under a force of about 1600 gram-weight, followed by suction of effusion under a reduced pressure of 400 mmHg. FIG. 7 shows the results of this test. As shown in FIG. 7, effusion could be collected over a period of one hour at a collection speed of 2.1 microliter/min. Since the amount of projection of the stylus from the front end of the needle body was 0.2 mm, the examinee did not experience any pain during the puncturing operation. Further, no bleeding was observed on the punctured skin.

Figure 8:
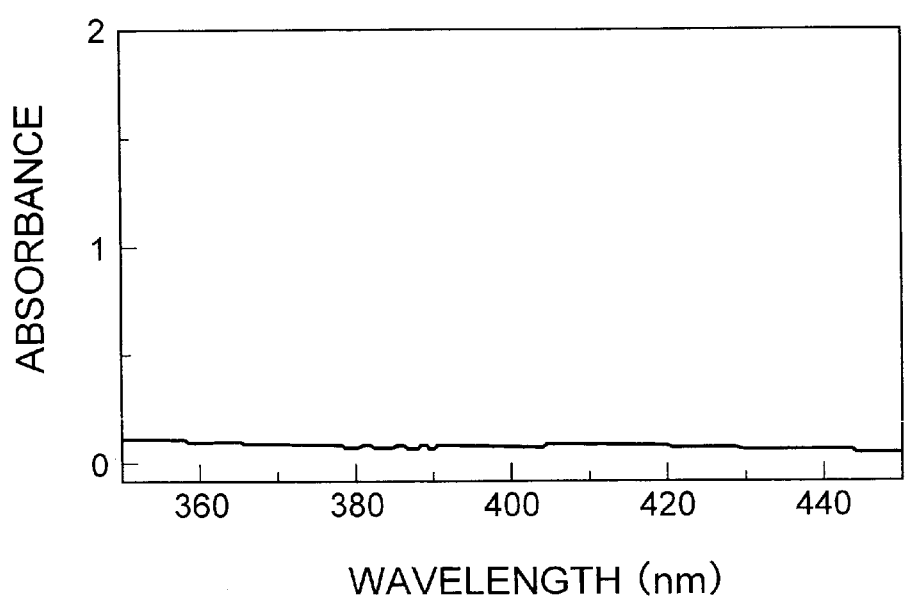
FIG. 8 is a graph showing an ultraviolet/visible-region absorption spectrum of collected effusion.

Further, the ultraviolet/visible-region absorption spectrum of the collected effusion was measured by use of a spectrophotometer Shimadzu UV-1200 product of Shimadzu Corp.). FIG. 8 shows the results of the measurement. As shown in FIG. 8, the absorbance did not increase in the vicinity of a wavelength of 414 nm. If the collected effusion contained blood, an absorption peak stemming from hemoglobin in the blood could be observed in the vicinity of the wavelength of 414 nm. The absence of the peak demonstrates that the effusion obtained by use of the corneum puncture member of the present invention contained no blood.

Since the above embodiments are described only for examples, the present invention is not limited to the above embodiments and various modifications or alterations can be easily made therefrom by those skilled in the art without departing from the scope of the present invention.

What is claimed is:

1. A corneum puncture device comprising a holder and a plurality of puncture needles arranged on said holder, each of said puncture needles having its own elongated columnar needle body mounted in said holder and a stylus extending from said needle body, a point of each stylus to be inserted into a corneum of a human body, wherein said stylus and said needle body form therebetween a stepped portion acting as a stopper when said stylus is inserted into a corneum of a human body, and wherein plural of adjacent ones of the puncture needles are aligned so that all of the stylus points of the plural adjacent needles are in a single row and together define a single, straight line.

2. A corneum puncture device comprising:

a stylus having a point, a base, and a tapered section intermediate the point and the base;

an elongated core attached at a first end to the base of said stylus; and a needle body enclosing each of the stylus and the core, said needle body being fixedly attached to said core preventing relative motion therebetween;

wherein said needle body encloses said base and a part of said tapered section of said stylus, and leaves a second end of said core extending from said needle body, and said stylus and said needle body form therebetween a stepped portion acting as a stopper when said stylus is inserted into a corneum of a human body.

3. The corneum puncture device of claim 2, wherein said needle body includes a first region covering, spaced apart from, and free of contact with the tapered section of said stylus.

4. The corneum puncture needle as defined in claim 3, wherein said needle body comprises a tube mechanically attached onto said core.

5. The corneum puncture needle as defined in claim 3, wherein said needle body comprises a tube adhered onto said core.

6. The corneum puncture needle as defined in claim 2, wherein said core comprises a spiral groove formed thereon.

7. The corneum puncture device of claim 2, wherein a first region of said needle body adjoins a second region of said needle body through an intermediate expanding region.

8. The corneum puncture device of claim 2, wherein a first thickness of said needle body, as measured perpendicular to a longitudinal axis of said needle body, in a region of said base is greater than a second thickness of said needle body, as measured perpendicular to the longitudinal axis, in a region surrounding said core.

9. The corneum puncture device of claim 2, wherein a thickness of the needle body perpendicular to a longitudinal axis of the needle body is uniform along the entire length of the needle body.

10. The corneum puncture device of claim 2, wherein said stylus and said core are comprised by a needle and said needle body is comprised by a tube press fitted to said core.

* * * * *